US012251526B2

(12) United States Patent
Modley et al.

(10) Patent No.: US 12,251,526 B2
(45) Date of Patent: Mar. 18, 2025

(54) MEDICAL ANCHOR DEVICE

(71) Applicant: University of Galway, Galway (IE)

(72) Inventors: Richard Modley, Plymouth (GB); Tim Jones, Galway (IE); Michelle Tierney, County Clare (IE)

(73) Assignee: UNIVERSITY OF GALWAY, Galway (IE)

( * ) Notice: Subject to any disclaimer, the term of this patent is extended or adjusted under 35 U.S.C. 154(b) by 780 days.

(21) Appl. No.: 17/415,423

(22) PCT Filed: Dec. 19, 2019

(86) PCT No.: PCT/EP2019/086306
§ 371 (c)(1),
(2) Date: Jun. 17, 2021

(87) PCT Pub. No.: WO2020/127731
PCT Pub. Date: Jun. 25, 2020

(65) Prior Publication Data
US 2022/0062591 A1 Mar. 3, 2022

(30) Foreign Application Priority Data
Dec. 21, 2018 (EP) .................... 18215406

(51) Int. Cl.
*A61M 39/02* (2006.01)
*A61M 25/02* (2006.01)

(52) U.S. Cl.
CPC ........ *A61M 25/02* (2013.01); *A61M 39/0208* (2013.01); *A61M 2025/0293* (2013.01);
(Continued)

(58) Field of Classification Search
CPC .. A61M 2039/0261; A61M 2039/0223; A61M 39/0247
See application file for complete search history.

(56) References Cited

U.S. PATENT DOCUMENTS

| 4,164,943 A | 8/1979 | Hill et al. |
| 5,496,283 A | 3/1996 | Alexander |

(Continued)

FOREIGN PATENT DOCUMENTS

| CN | 106999178 A | 8/2017 |
| EP | 0542103 A1 | 5/1993 |

(Continued)

OTHER PUBLICATIONS

International Search Report and Written Opinion in corresponding Application No. PCT/EP2019/086306, dated Feb. 26, 2020, (17 pages).

(Continued)

*Primary Examiner* — Deanna K Hall
(74) *Attorney, Agent, or Firm* — Bookoff McAndrews, PLLC

(57) ABSTRACT

A medical anchor device (1) for securing a medical article to a subject comprising an upper medical article attachment portion (2) and a lower insertion portion (3) for securing the medical anchor device (1) to the subject wherein the insertion portion (3) comprises a spiral anchor (5) so that the medical anchor device (1) is securable to and detachable from the subject by rotating the medical anchor device (1) in a clockwise or an anti-clockwise manner as required by the direction of the spiral anchor (5).

12 Claims, 5 Drawing Sheets

(52) U.S. Cl.
CPC .............. *A61M 2039/0223* (2013.01); *A61M 2039/0232* (2013.01)

(56) References Cited

U.S. PATENT DOCUMENTS

| | | | |
|---|---|---|---|
| 5,685,859 | A | 11/1997 | Kornerup |
| 6,056,769 | A * | 5/2000 | Epstein ............ A61B 17/00491 606/213 |
| 6,544,272 | B1 | 4/2003 | Jakob et al. |
| 7,959,615 | B2 | 6/2011 | Stats et al. |
| 9,468,740 | B2 | 10/2016 | Bierman et al. |
| 2004/0143237 | A1 * | 7/2004 | Hart ...................... A61M 25/04 604/506 |
| 2006/0079845 | A1 | 4/2006 | Howard et al. |
| 2006/0106295 | A1 | 5/2006 | Jais et al. |
| 2008/0154296 | A1 | 6/2008 | Taylor et al. |
| 2012/0078191 | A1 | 3/2012 | Rosenberg et al. |
| 2015/0094577 | A1 | 4/2015 | Saadat et al. |

FOREIGN PATENT DOCUMENTS

| | | |
|---|---|---|
| EP | 0663184 A1 | 7/1995 |
| EP | 3284412 A1 | 2/2018 |
| ES | 2366188 T3 | 10/2011 |
| JP | 2006519084 A | 8/2006 |
| JP | 2017536172 A | 12/2017 |
| WO | 2016087934 A1 | 6/2016 |

OTHER PUBLICATIONS

CN Office Action in corresponding Application No. 201980089943.7, dated Apr. 8, 2023, (8 pages).
English Translation of Japanese Office Action issued in corresponding JP Application No. 2021-535591, dated Oct. 12, 2023, (3 pages).
JP Office Action in corresponding Japanese Application No. 2021-535591, dated Apr. 12, 2024, (3 pages).

* cited by examiner

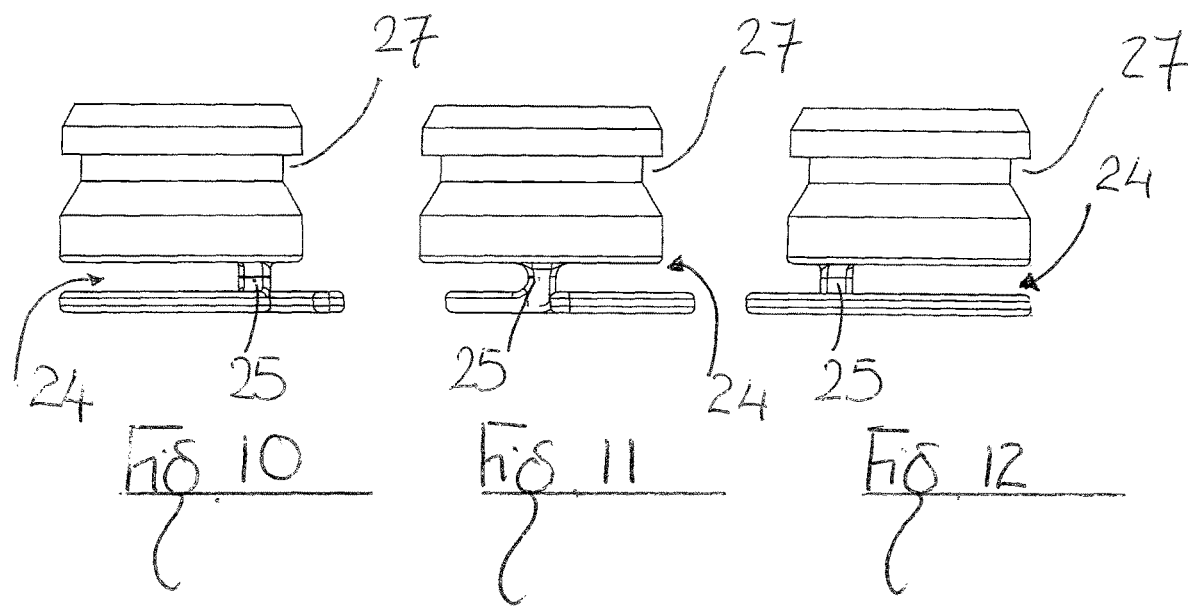

MEDICAL ANCHOR DEVICE

This invention relates to a medical anchor device for securing a medical article to a subject. More particularly, the invention relates to a medical anchor device for securing elongate medical articles such as catheters, ports, pumps and tubes to a subject. The invention also relates to a medical anchoring system comprising the medical anchor device and the medical article and to a method for securing a medical article to a subject.

BACKGROUND OF THE INVENTION

The appropriate securement of medical articles to a subject is critical to ensure optimal performance of the medical article. For example, a range of therapeutic areas require the securement of medical articles such as catheters or tubing to a subject for fluid drainage, bariatric therapies, waste excretion management, feeding, and intraperitoneal administration of therapeutics. In such treatments, it is imperative to mitigate the potential risks of catheter/tubing issues such as dislodgement, infection or blockage. As a result, a variety of securing methodologies are currently used across these therapeutic areas ranging from balloon anchors, sutures, adhesives, pigtail anchoring and relatively invasive subcutaneous methods.

For example, U.S. Pat. Nos. 4,164,943, 7,959,615, 2012/078191, 2006/079845, 5,496,283, 5,685,859 and 9,468,740 describe a range of medical device retainers and systems all of which either require the use of adhesives, sutures, require relatively complex surgical procedures to secure the medical device retainer to a subject and/or are highly invasive and bore deeply into a subject. Adhesive fixings are known to fail over time and can give rise to severe allergic reactions while the need to use sutures and complex surgical procedures requiring multiple incisions to secure the medical device retainer can be time consuming and result in subject discomfort. In addition, many of the known medical device retainers of the prior art are complex devices that can also be expensive to manufacture, are difficult to use and require surgical dexterity to deploy correctly.

In summary, various differing mechanisms are employed to secure medical articles such as catheters, many of which are specific to individual therapeutic areas and anatomical locations, require invasive placement procedures, or are only compatible with certain catheter types.

An object of the invention is to overcome at least some of the problems of the prior art.

In this specification, reference is made to a medical anchor device for use with subjects. As will be appreciated by those skilled in the art, the medical anchor device of the invention is suitable for use with human and animal subjects. Accordingly, the medical anchor can be used in human and veterinary medicine and reference to medicine and subjects should be construed to include human and animal medicine and subjects.

SUMMARY OF THE INVENTION

According to the invention there is provided a medical anchor device for securing a medical article to a subject comprising:
an upper medical article attachment portion and
a lower insertion portion for securing the medical anchor device subcutaneously to a subject wherein the insertion portion comprises a spiral anchor disposed substantially in a single plane.

In one embodiment, the spiral anchor (5) defines an Archimedean spiral shape. i.e. the spiral anchor is disposed in a single plane.

Preferably, the spiral anchor extends laterally outwards from the medical article attachment portion.

In one embodiment, the spiral anchor comprises at least one full turn.

Preferably, the spiral anchor is flexible.

Preferably, the spiral anchor comprises a free insertion end for insertion in a subject.

In one embodiment, the medical anchor device further comprises a skin receiving interstice between the medical article attachment portion and the spiral anchor. Preferably, the interstice comprises a slot-like interstice. Suitably, the interstice is defined by a spacer arm between the medical article attachment portion and the spiral anchor. More preferably, the spacer arm is configured to define a curved skin abutting face.

In one embodiment, the curved skin abutting face comprises a concave skin abutting face.

Preferably, the spacer arm comprises a non-flexible spacer arm.

Suitably, the spiral anchor is attached to the medical article attachment portion at a medical article attachment portion end contiguous with the medical article attachment portion.

In one embodiment, the medical article attachment portion comprises a platform. Preferably, the platform comprises a substantially cylindrical platform. More preferably, the platform comprises a lumen. The cylindrical platform may have a cross-section that is generally circular, oval, square, rectangular or any other shape.

In one embodiment, the medical article attachment portion comprises adhesive for adhering the attachment portion to the subject around an incision.

Most preferably, the lumen comprises a top opening and a bottom opening.

Advantageously, the platform comprises a medical article mounting. Preferably, the medical article mounting comprises a top medical article mounting at the top opening.

Optionally or in addition, the medical article mounting comprises a bottom medical article mounting at the bottom opening.

In one embodiment, the top medical article mounting and/or the bottom medical article mounting comprises a screw thread. Other forms of mountings may be employed, such as for example re-entrant slots, friction-fit mountings, adhesive mountings, and clips or clamps.

In one embodiment, the medical anchor device is a unitary medical anchor device.

Alternatively, the medical anchor device 1 is a multi-part medical anchor device.

The medical article is generally a medical device having a part that is inserted into the body. Examples include elongate tubular articles such as catheters and drainage tubes. In a preferred embodiment of the invention, the medical anchor device is a catheter anchor device. Other articles include pumps, ports and sensors for which it is advantageous to anchor to the skin.

The invention also extends to a medical anchoring system for securing a medical article to a subject (typically the skin of a subject) comprising a medical anchor device as hereinbefore defined and a medical article engageable with the medical anchor.

In a preferred embodiment, the medical article consists of or includes an elongate element engageable with the medical anchor, for example a catheter or drainage tube. In other embodiments, the part of the medical article that engages with the anchor is not an elongate element, and may be for example a pump, sensor or the like. In one embodiment, the anchor and medical article comprise formations configured for inter-engagement to lock the article to the anchor, for example threads, friction-fit formations, or re-entrant slot formations.

In a further embodiment, the invention also extends to a method for securing a medical article to a subject (typically the skin of a subject) with a medical anchor device as herein before defined.

In one embodiment, the invention relates to a method for attaching a medical article to a subject by securing it subcutaneously with a medical anchor device comprising creating an incision in the subject at an insertion site;

inserting a medical anchor device having an upper medical article attachment portion and a lower insertion portion, in which the insertion portion comprises a spiral anchor disposed substantially in a single plane, in the incision by inserting an insertion end of the spiral anchor in the incision, and rotating the medical anchor device subcutaneously in the incision to secure the medical anchor device to the subject.

Preferably, a single incision is created at the insertion site. More preferably, the single incision is a subcutaneous single incision.

In one embodiment, the device is rotated through at least one half of a turn (180°), three-quarters of a turn (270°), or at least one full turn (360°).

Suitably, the medical anchor device is rotated in a clockwise or anti-clockwise manner depending on the direction of the spiral anchor.

Preferably, the medical anchor device is fully inserted after one full rotation.

The method further comprises the step of attaching a medical article to the medical attachment portion.

The medical anchor device of the invention is universally applicable for medical article securement across a range of therapeutic areas. The medical anchor device is particularly suitable for the securement and fixing in place of catheters and other elongate or tubular articles which are widely used and particularly prone to dislodgement so that a highly efficacious medical anchoring system made up of the medical device anchor and catheters engageable with the medical device anchor is also provided by the invention.

Generally, the invention therefore provides a medical anchor device for securing a medical article to a subject comprising an upper medical article attachment portion and a lower insertion portion for securing the medical anchor device to a subject wherein the insertion portion comprises a spiral anchor.

The medical anchor device is a simple, non-boring, minimally invasive, comfortable, subcutaneous medical article/catheter anchor that can be applied to multiple anatomical locations and accommodate multiple medical article/catheter types. In particular, the flexible spiral anchor of the medical anchor device facilitates secure anchoring in tissue via a single, subcutaneous incision point to ensure that the medical anchor device is centrally located with respect to the incision point so that the incision is positioned centrally within the lumen of the platform.

The subcutaneous medical anchor device of the invention therefore enjoys a number of advantages over the prior art in that it:

ensures a streamlined way of anchor placement;
requires less procedural time to place compared to current invasive securement methods;
does not require sutures;
does not require adhesives (although adhesive may be additionally employed);
has superior securing ability;
has a simple but effective unitary structure;
is cost-effective to manufacture;
has universality—is suitable for use across a range of medical articles and therapeutic uses but is particularly suitable for universal use with catheters and the like of all types;
is comfortable for subjects, and
is easier to remove compared to known invasive securement methods.

All publications, patents, patent applications and other references mentioned herein are hereby incorporated by reference in their entireties for all purposes as if each individual publication, patent or patent application were specifically and individually indicated to be incorporated by reference and the content thereof recited in full.

Definitions and General Preferences

Where used herein and unless specifically indicated otherwise, the following terms are intended to have the following meanings in addition to any broader (or narrower) meanings the terms might enjoy in the art:

Unless otherwise required by context, the use herein of the singular is to be read to include the plural and vice versa. The term "a" or "an" used in relation to an entity is to be read to refer to one or more of that entity. As such, the terms "a" (or "an"), "one or more," and "at least one" are used interchangeably herein.

As used herein, the term "comprise," or variations thereof such as "comprises" or "comprising," are to be read to indicate the inclusion of any recited integer (e.g. a feature, element, characteristic, property, method/process step or limitation) or group of integers (e.g. features, element, characteristics, properties, method/process steps or limitations) but not the exclusion of any other integer or group of integers. Thus, as used herein the term "comprising" is inclusive or open-ended and does not exclude additional, unrecited integers or method/process steps.

As used herein, the term "disease" is used to define any abnormal condition that impairs physiological function and is associated with specific symptoms. The term is used broadly to encompass any disorder, illness, abnormality, pathology, sickness, condition or syndrome in which physiological function is impaired irrespective of the nature of the aetiology (or indeed whether the aetiological basis for the disease is established). It therefore encompasses conditions arising from infection, trauma, injury, surgery, radiological ablation, poisoning or nutritional deficiencies.

In the context of methods of securing the device of the invention as defined above, the term subject (which is to be read to include "individual", "animal", "patient" or "mammal" where context permits) defines any subject, particularly a mammalian subject, for whom treatment is indicated. Mammalian subjects include, but are not limited to, humans, domestic animals, farm animals, zoo animals, sport animals, pet animals such as dogs, cats, guinea pigs, rabbits, rats, mice, horses, cattle, cows; primates such as apes, monkeys, orangutans, and chimpanzees; canids such as dogs and wolves; felids such as cats, lions, and tigers; equids such as horses, donkeys, and zebras; food animals such as cows, pigs, and sheep; ungulates such as deer and giraffes; and rodents such as mice, rats, hamsters and guinea pigs. In preferred embodiments, the subject is a human.

BRIEF DESCRIPTION OF THE DRAWINGS

The invention will now be described, by way of example only, with reference to the accompanying drawings in which:

FIG. 10 is a side elevation of the medical anchor device;

FIG. 11 is a partially rotated side elevation of the medical anchor device, and

FIG. 12 is a fully rotated side elevation of the medical anchor device.

DETAILED DESCRIPTION OF THE INVENTION

Figure 1:
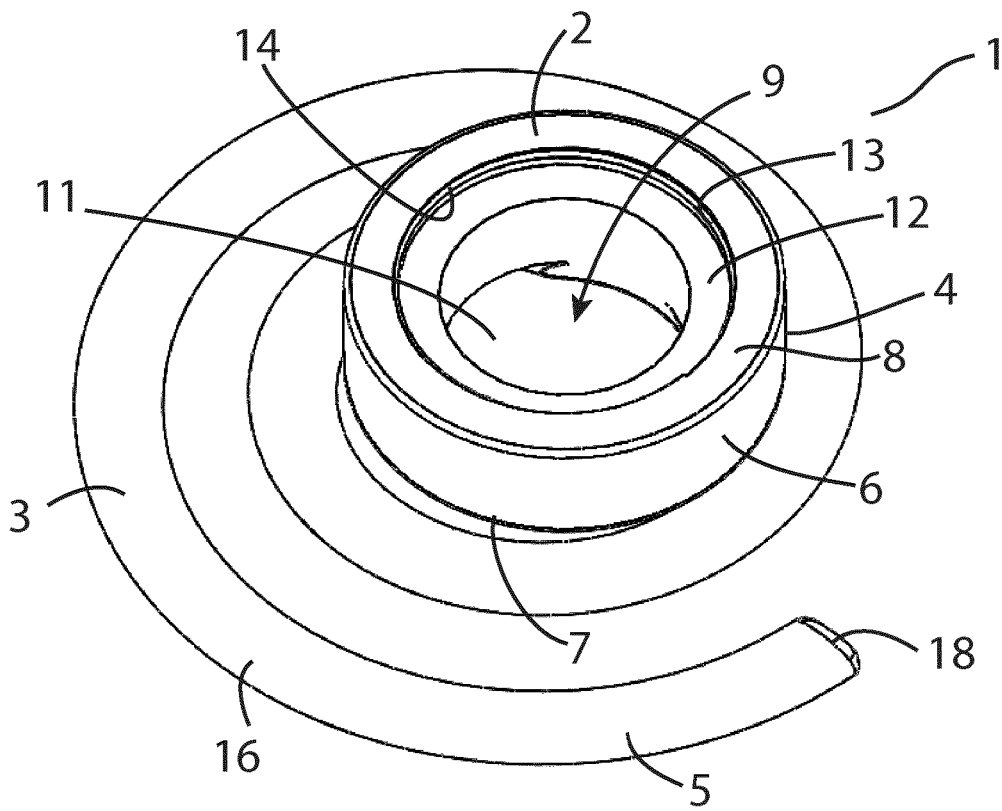
FIG. 1 is a perspective view from above and one side of a first embodiment of a medical anchor device in accordance with the invention having a medical article attachment portion and a spiral or helical anchor for securely inserting the medical anchor device in a subject and securing a medical article to the medical anchor device and subject.
Figure 2:
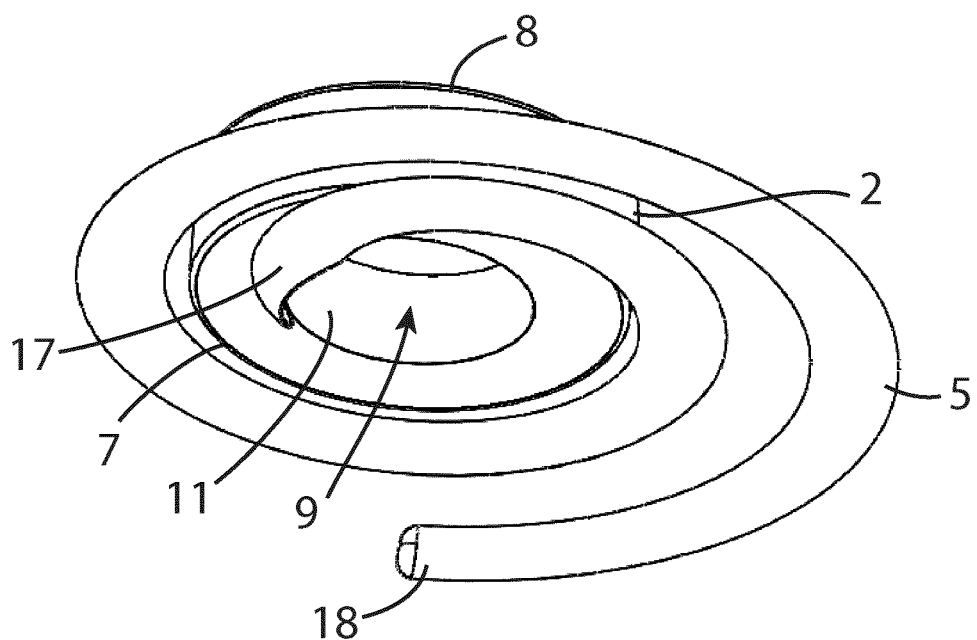
FIG. 2 is a perspective view from above and one side of the underside of the medical anchor device.

As shown in the drawings, a medical anchor device for securing a medical article to a subject is indicated by the reference numeral 1 and generally comprises an upper medical article attachment portion 2 for receiving medical articles such as catheters, tubes and the like and a lower insertion portion 3 for subcutaneous insertion in a subject to secure the medical anchor device 1 to the subject. More particularly, the medical article attachment portion 2 is made up of a cylindrical platform 4 while the insertion portion 3 is made up of a substantially flat spiral anchor 5 having a substantially flat pitch to prevent boring into a subject—i.e. the spiral anchor 5 is substantially in a single plane so that the spiral anchor 5 is non-boring. The spiral anchor 5 is therefore adapted to enter the skin to an incision depth which is typically approximately equivalent to median skin depth i.e. the spiral anchor is positioned under the dermis. The spiral anchor 5 therefore anchors the medical anchor device 1 of the invention subcutaneously (i.e. under the dermis) by distributing an anchoring force in a lateral horizontal plane defined by the spiral anchor 5 rather than a vertical anchoring force boring into the skin. Accordingly, the spiral anchor 5, and in particular the elongate body 16 creates and defines a planar or Archimedean spiral shaped channel in the fatty tissue (hypodermis) below the dermis and the epidermis to anchor the medical anchor device 1 of the invention below the skin. If desired, the channel for receiving the elongate body 16 can also be created via the incision with a scalpel.

In the present embodiment, the spiral anchor 5 also extends laterally outwards from the cylindrical platform 4 to further increase the horizontal anchoring force. The spiral anchor 5 is rotatably insertable in a subject in a clockwise or an anti-clockwise manner as required by the direction of the spiral anchor 5 to secure the medical anchor device 1 to the subject without excessive boring into the subject and is detachable from the subject by reversibly rotating the medical anchor device 1.

The cylindrical platform 4 is made up of a circular sidewall 6 having a bottom edge 7 disposed towards the spiral anchor 5, a top edge 8 and a central lumen 9 extending between the bottom and top edges 7,8 respectively to define a bottom opening 10 and a top opening 11 in the cylindrical platform 4 so that medical articles and equipment can be passed through the central lumen 9 via the bottom and top openings 10,11 respectively.

The top edge 8 of the cylindrical platform 4 is provided with a top medical article mounting or fitting 12 at the top opening 11 for securing external medical articles to the medical device anchor 1. The top mounting or fitting 12 can be shaped or configured as required in accordance with the type and size of medical article to be attached to the medical device anchor 1. In the present embodiment, the top mounting 12 is in the form of a recessed groove 13 defined in the top edge 8 which is provided with a screw thread 14 for attachment to a complementary fitting on a medical article.

Similarly, the bottom edge 7 of the cylindrical platform 4 is provided with a bottom medical article mounting or fitting 15 at the bottom opening 10 for securing medical articles such as an internal catheter or tube to the medical anchor device 1.

The spiral anchor 5 of the insertion portion 3 is made up of a coiled elongate body 16 having a medical article attachment portion or platform end 17 attached to the cylindrical platform 4 and a free insertion end 18 for insertion in a subject. More particularly, in the present embodiment, the platform end 17 is contiguous with the bottom edge 7 of the cylindrical platform 4 while the coiled elongate body 16 winds outwards from the bottom edge 7 to terminate at the insertion end 18. The length of the coiled elongate body 16 can be sized as required. The spiral anchor 5 can be formed with a clockwise or anti-clockwise spiral as required, and, as indicated above is typically disposed in a substantially single plane to prevent excessive boring into a subject. Accordingly, the arrangement of, in particular, the elongate body 16 of the spiral anchor 5 in a single plane allows subcutaneous penetration by the spiral anchor 5, generally to a median subcutaneous skin depth or thickness defined by an incision depth, which is sufficient for the medical anchor device 1 to be reversibly anchored to a subject's skin but without boring in an invasive manner into the subject.

The spiral anchor 5 is sufficiently rigid to allow it to be rotated in tissue and create the spiral-shaped channel corresponding with the spiral of the spiral elongate body 16 so that the spiral anchor 5 can enter into the tissue without excessive boring. In one embodiment, the spiral elongate body 16 is also sufficiently compliant or flexible to allow the medical anchor device 1, and in particular the central lumen 9 to be in a centred position with respect to the incision point when fully inserted. More particularly, the flexibility of the elongate body 16 ensures that the incision point is centrally positioned within the lumen 9 in the fully inserted position. Although the Applicant does not wish to be bound by any theorem, it is believed that the flexibility of the elongate body 16 allows the spiral anchor 5 spiral/flex slightly downwardly and/or outwardly when in a fully inserted position to centrally anchor the medical anchor device 1 with respect to the incision point. This allows for easy and unobstructed insertion of medical devices through the incision point.

Figure 3:
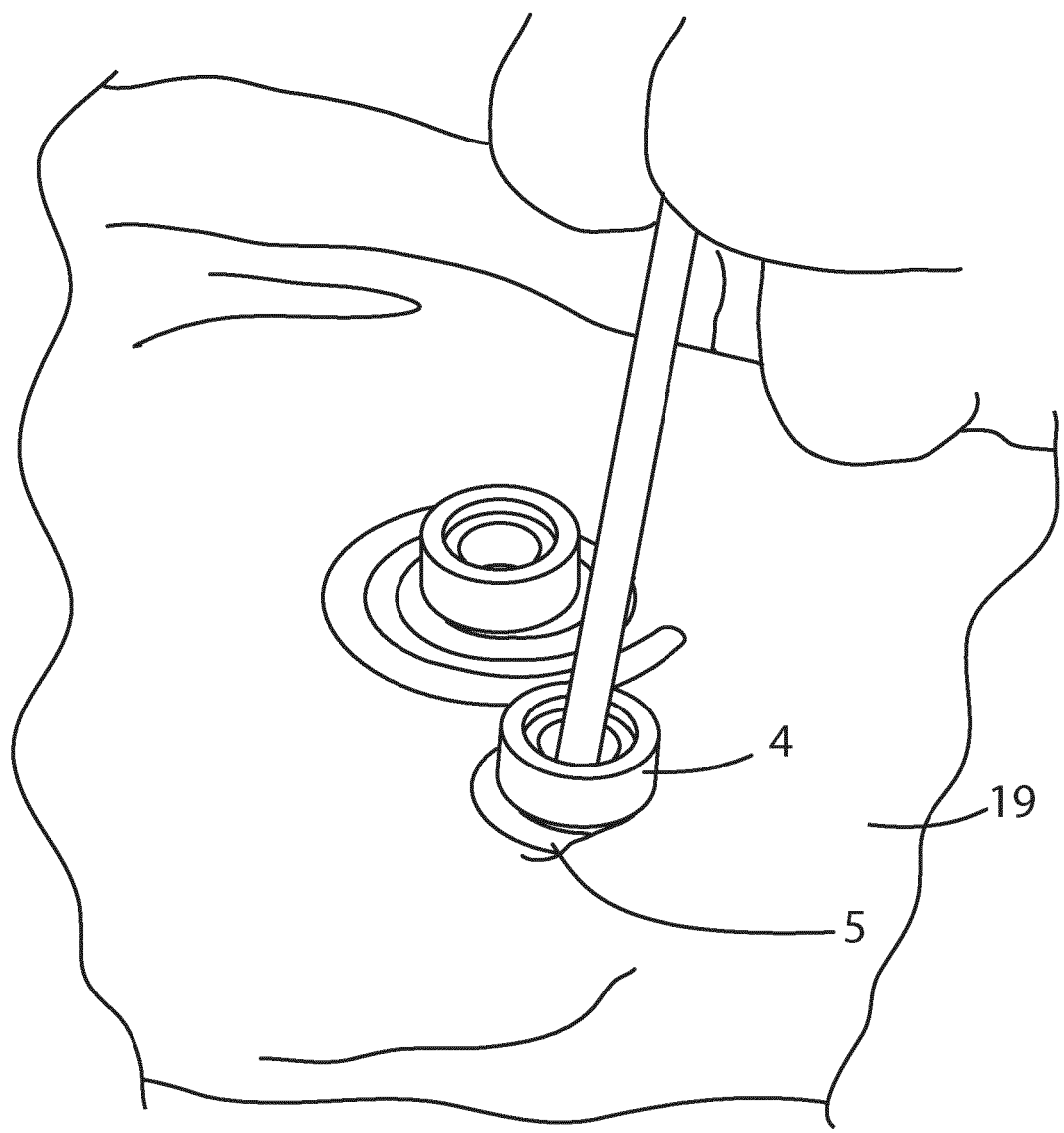
FIG. 3 is an image from above and one side of a first medical anchor device placed on a subject prior to insertion at an insertion site in the subject and of a second medical anchor device with the spiral anchor of the medical anchor device inserted in the subject at an insertion site defined by a single incision mark visible through the lumen of the medical anchor device.
Figure 4:
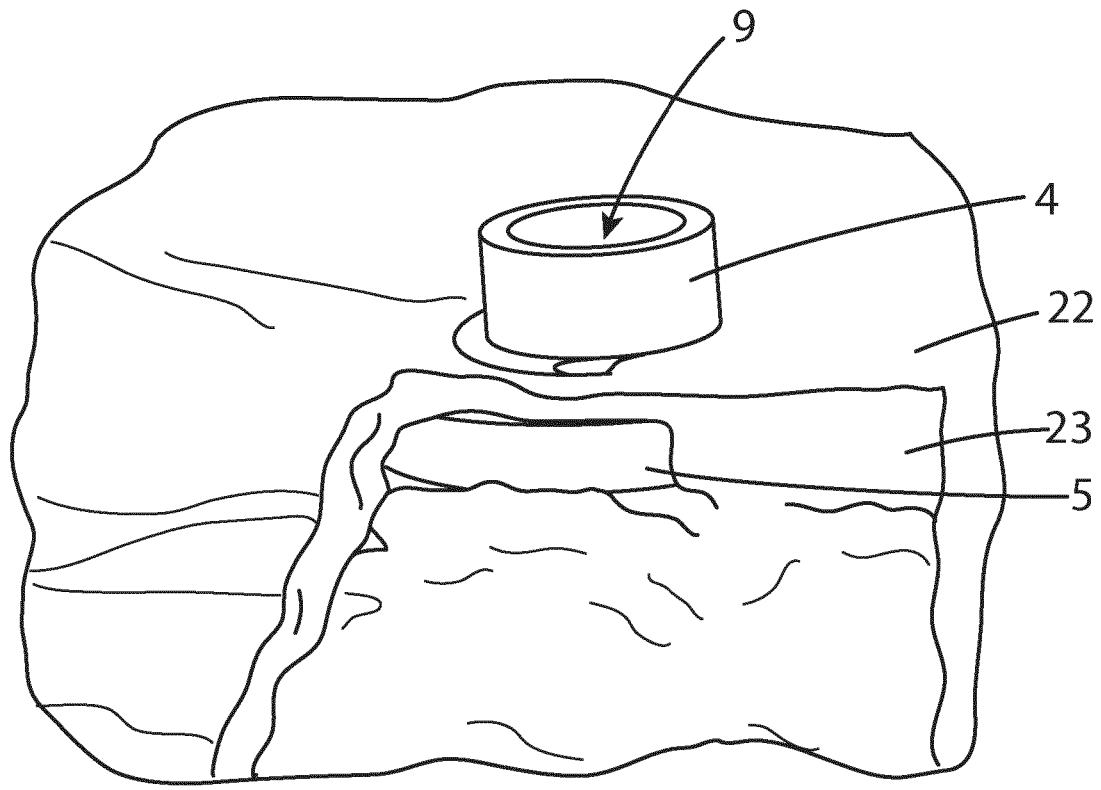
FIG. 4 is a side image of the post-insertion medical anchor device of FIG. 3 with the outer skin layers partially cutaway to reveal the spiral anchor secured in the subcutaneous layer (hypodermis) of the subject.
Figure 5:
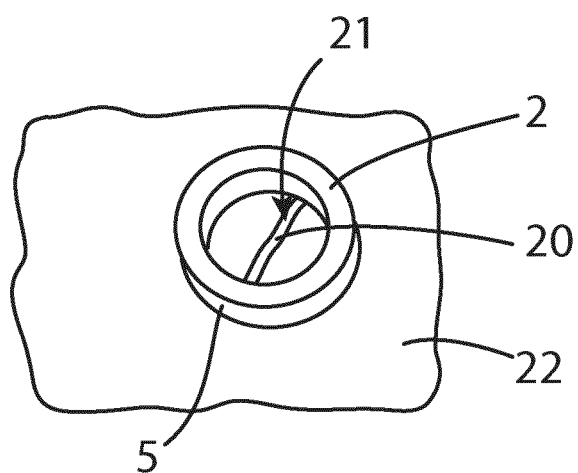
FIG. 5 is an enlarged image from above of the post-insertion medical anchor device of FIGS. 3 and 4 with the incision mark visible through the lumen.
Figure 8:
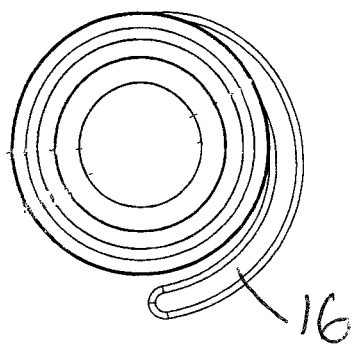
FIG. 8 is a top plan view of the medical anchor device.
Figure 6:
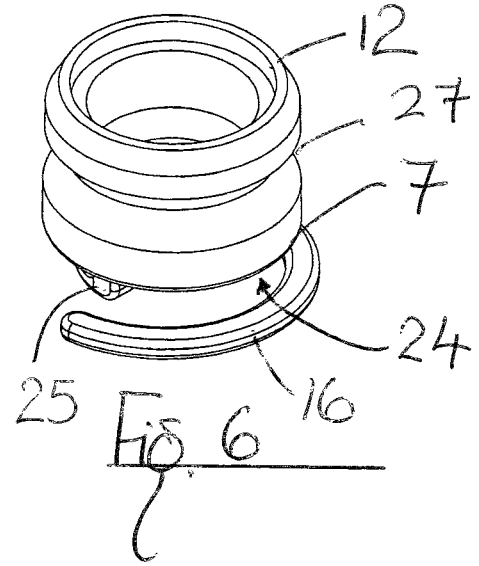
FIG. 6 is a perspective view from above and one side of a second embodiment of a medical anchor device in accordance with the invention in which the device is provided with space in the form of a slot-like interstice defined by a spacer arm between the medical article attachment portion and the spiral anchor for receiving and a subject's skin.
Figure 7:
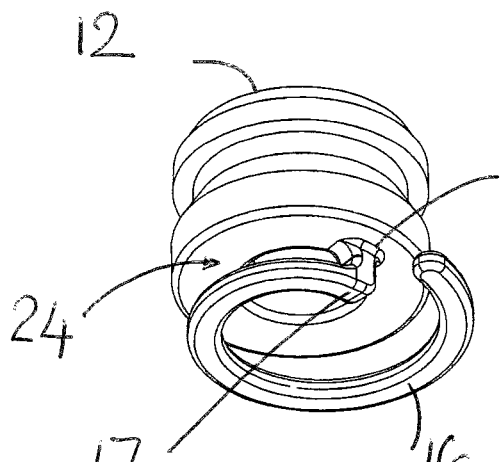
FIG. 7 is a perspective view from below and one side of the medical anchor device of FIG. 6.
Figure 9:
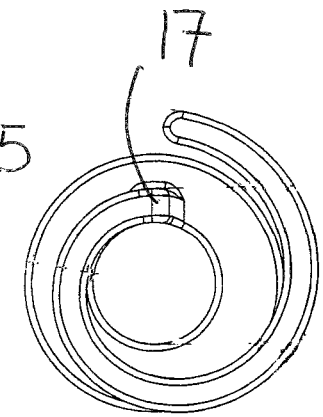
FIG. 9 is a bottom plan view of the medical anchor device.

As shown particularly in FIGS. 3 to 5, in use, the medical anchor device 1 can be secured to the body 19 of a subject by creating one subcutaneous incision 20 at an insertion site 21 on the skin 22 of the subject. The insertion end 18 of the spiral anchor 5 is then placed into the incision 20 and, by gripping and turning the cylindrical platform 4, the coiled elongate body 16 of the spiral anchor 5 is rotated in a generally single horizontal plane through the subcutaneous layer 23 to embed and anchor the medical device anchor 1 in the subject usually to a depth determined by the incision. When fully rotated, the incision 20 at the insertion site, being centrally located with respect to the spirally winding elongate body 16 of the spiral anchor 5, becomes visible through the top opening 11 and central lumen 9 of the cylindrical platform 4.

Medical articles such as catheters and the like can then be inserted through the central lumen 9 and the incision 20 at the insertion site 21 as required.

The subcutaneously inserted medical anchor device 1 therefore acts as a platform onto which further components can be added to the medical article attachment portion 2 as required depending on the intended therapeutic use or medical article type employed.

The medical anchor device 1 of the invention can also be simply removed by rotating the spiral anchor 5 in the opposite direction without requiring invasive surgical intervention such as is required with retainers and the like of the prior art where sutures or the retainers themselves must be surgically extracted from a subject.

FIGS. 6 to 12 show a second embodiment of a medical anchor device 1 broadly similar to the medical anchor device 1 of FIGS. 1 to 5 and like numerals indicate like parts. However, in the present embodiment, the medical anchor device 1 is provided with a skin receiving interstice 24 between the medical article attachment portion 2 and the spiral anchor 5 for receiving a subject's skin between the medical article attachment portion 2 and the spiral anchor 5. The interstice 24 is slot-like in construction and is defined by the bottom edge 7 of the cylindrical platform 4 and the coiled elongate body 16 of the spiral anchor 5. More particularly, the coiled elongate body 16 is spaced apart from the bottom edge 7 of the cylindrical platform 4 by a downwardly depending spacer arm 25 extending between the platform end 17 of the coiled elongate body 16 and the bottom edge 7 of the cylindrical platform 4 to define the interstice 24. The width of the interstice 24 is therefore determined by the size of the spacer arm 25 which is usually sized so that the interstice 24 can receive a skin layer of median thickness without damaging or pinching the skin i.e. without causing discomfort to a subject. The spacer arm 25 can be formed from a material which has no flexibility, unlike the spiral anchor 5, so that the spacer arm 25 also serves as a reinforcing spacer arm 25 to reinforce the spiral anchor 5 during insertion in a subject.

The spacer arm 25 is also configured to define a concave curved face 26 disposed inwards towards the interstice 24 between the platform end 17 of the coiled elongate body 16 and the bottom edge 7 of the cylindrical platform 4. The curved face 26 serves as an abutting surface or a stop to abut against skin received in the interstice 24 following full insertion of the medical anchor device 1. The concave curved face 26 also prevents pinching of the skin to further enhance a subject's comfort. Moreover, the Applicant has found that the curved face 26 also reinforces the spacer arm 25 and the overall strength of the medical anchor device 1 during insertion.

In the present embodiment, the elongate body 16 of the spiral anchor 16 is sized to be of reduced length when compared with the elongate body 16 of FIGS. 1 to 5 so that the spiral anchor 5 is fully inserted after one full rotation of the medical anchor device 1 further reducing the invasiveness of the device 1.

In addition, in the present embodiment, the circular sidewall 6 of the cylindrical platform 4 is shaped to define a waist 27 to provide a secondary medical article mounting or fitting on the cylindrical platform 4.

The medical anchor device 1 of the invention can be formed from any suitable material or combination of materials e.g. the spiral anchor 5 can be formed from resilient or elastomeric materials having a desired degree of flexibility e.g. Santoprene (Trade Mark) while the leg 25 and/or the medical article attachment portion can be formed from non- or less resilient materials.

The medical anchor device 1 can also be sized as required in accordance with the size and/or level of support required by the medical articles to be attached to the medical anchor device 1. For example, in the case of medical anchor devices 1 for use in supporting catheters, the medical anchor device of FIGS. 6 to 12 could be sized so that the distance between the leg 25 and the diametrically opposite bottom edge 7 of the cylindrical platform 4 corresponds with the incision length generally employed for the insertion of catheters e.g. between about 10 mm and about 20 mm.

While the medical anchor device 1 of the invention can be formed as a unitary medical anchor device 1 i.e. as a single unit, the medical anchor device 1 can also be formed as a multi-part device if desired e.g. the medical anchor device 1 can be made up of two or more parts such as a medical attachment portion 2 attachable to a lower insertion portion 3.

The medical anchor device 1 can also form part of a medical anchoring system in accordance with the invention made up of the medical anchor device 1 and a medical article such as a catheter engageable with the medical anchor device 1.

The invention claimed is:

1. A medical anchor device for securing a medical article to a subject comprising:
   an upper medical article attachment portion;
   a lower insertion portion for securing the medical anchor device subcutaneously to a subject wherein the insertion portion comprises a spiral anchor disposed substantially in a single plane; and
   a skin receiving interstice between the medical article attachment portion and the spiral anchor, the interstice defined by a spacer arm between the medical article attachment portion and the spiral anchor, wherein the spiral anchor winds laterally outwards from the medical article attachment portion.

2. A medical anchor device as claimed in claim 1 wherein the spiral anchor defines an Archimedean spiral shape.

3. A medical anchor device as claimed in claim 1 wherein the spiral anchor is flexible.

4. A medical anchor device as claimed in claim 1 wherein the spiral anchor comprises a free insertion end for insertion in a subject.

5. A medical anchor device as claimed in claim 1 wherein the spacer arm is configured to define a curved skin abutting face.

6. A medical anchor device as claimed in claim 1 wherein the spiral anchor is attached to the medical article attachment portion at a medical article attachment portion end contiguous with the medical article attachment portion.

7. A medical anchor device as claimed in claim 1 wherein the medical article attachment portion comprises a platform.

8. A medical anchor device as claimed in claim 7 wherein the platform comprises a lumen.

9. A medical anchor device as claimed in claim 7 wherein the platform comprises a medical article mounting.

10. A medical anchor device as claimed in claim 1 wherein the medical anchor device is a catheter anchor device.

11. A medical anchoring system for securing a medical article to a subject comprising a medical anchor device as claimed in claim 1 and a medical article engageable with the medical anchor device.

12. A medical anchoring system for securing a medical article to a subject as claimed in claim 11 wherein the medical anchor device and the medical article comprise formations configured for inter-engagement to lock the medical article to the medical anchor device.

* * * * *